(12) United States Patent
Mukai et al.

(10) Patent No.: US 10,052,238 B2
(45) Date of Patent: Aug. 21, 2018

(54) METHOD OF MANUFACTURING PANTS-TYPE DIAPER

(71) Applicant: UNICHARM CORPORATION, Shikokuchuo-shi, Ehime (JP)

(72) Inventors: Hirotomo Mukai, Kanonji (JP); Akihide Ninomiya, Kanonji (JP); Akihisa Shiomi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 141 days.

(21) Appl. No.: 15/271,228

(22) Filed: Sep. 21, 2016

(65) Prior Publication Data

US 2017/0087028 A1 Mar. 30, 2017

(30) Foreign Application Priority Data

Sep. 28, 2015 (JP) ................................. 2015-190129

(51) Int. Cl.
 *A61F 13/15* (2006.01)
 *A61F 13/496* (2006.01)
 (Continued)

(52) U.S. Cl.
 CPC .. *A61F 13/15593* (2013.01); *A61F 13/15699* (2013.01); *A61F 13/15723* (2013.01);
 (Continued)

(58) Field of Classification Search
 CPC .......... A61F 13/15593; A61F 13/15699; A61F 13/15723; A61F 13/15739; A61F 13/15764
 See application file for complete search history.

(56) References Cited

U.S. PATENT DOCUMENTS 7,740,732 B2 * 6/2010 Umebayashi ..... A61F 13/15699
 156/269
8,440,043 B1 * 5/2013 Schneider ......... A61F 13/15723
 156/160
(Continued)

FOREIGN PATENT DOCUMENTS

EP 1188427 A1 3/2002
EP 1661535 A1 * 5/2006
(Continued)

OTHER PUBLICATIONS

Office Action in EP Application No. 16188299.8, dated Oct. 20, 2017, 7pp.
(Continued)

*Primary Examiner* — Jeffry H Aftergut
(74) *Attorney, Agent, or Firm* — Hauptman Ham, LLP (57) ABSTRACT

A method of manufacturing a pants-type diaper comprises: a step (A) of conveying a first continuous sheet; a step (B) of laminating a plurality of continuous elastic bodies on an inner side of the first continuous sheet, laminating a second continuous sheet, and bonding at least a part of the continuous elastic bodies and the second continuous sheet; a step (C) of cutting a part of continuous elastic bodies from an outer side of the second continuous sheet or an outer side of the first continuous sheet; and a step (D) of disposing the absorbent body so as to arrange the absorber in a predetermined region. In the step (C), a part of the continuous elastic bodies that is not bonded to the first continuous sheet is cut in a region for forming the pants-type diaper, the region other than a predetermined region for arranging the absorber.

12 Claims, 6 Drawing Sheets

(51) Int. Cl.
*B32B 38/00* (2006.01)
*B32B 43/00* (2006.01)

(52) U.S. Cl.
CPC .. *A61F 13/15739* (2013.01); *A61F 13/15764* (2013.01); *A61F 13/496* (2013.01); *B32B 38/0004* (2013.01); *B32B 43/003* (2013.01); *B32B 2555/02* (2013.01)

(56) References Cited

U.S. PATENT DOCUMENTS

2006/0244166 A1* 11/2006 Wada ................ A61F 13/15593
264/37.1
2009/0283207 A1* 11/2009 Tachibana ......... A61F 13/15593
156/209

FOREIGN PATENT DOCUMENTS

| EP | 2979670 A1 | | 2/2016 |
|---|---|---|---|
| JP | 2004-298362 A | | 10/2004 |
| JP | 2009-172231 A | * | 8/2009 |
| JP | 2013-138795 A | | 7/2013 |
| JP | 2014-221122 A | | 11/2014 |
| WO | 2008/041639 A1 | | 4/2008 |
| WO | 2009/119139 A1 | | 10/2009 |
| WO | 2014/156949 A1 | | 10/2014 |

OTHER PUBLICATIONS

Extended European Search Report in EP Application No. 16188299.8, dated Feb. 22, 2017.
Office Action in JP Application No. 2015-190129, dated Apr. 3, 2018, 13pp.

* cited by examiner

METHOD OF MANUFACTURING PANTS-TYPE DIAPER

RELATED APPLICATIONS

The present application claims priority to Japanese Patent Application Number 2015-190129 filed Sep. 28, 2015, the disclosure of which is hereby incorporated by reference herein in its entirety.

BACKGROUND

Technical Field

The present invention relates to a method of manufacturing a pants-type diaper.

Related Art

A pants-type diaper known in the art includes an elastic member (elastic member for fit gathers) which is stretchable in the width direction of a front waist member. In such a known pants-type diaper, the elastic member is cut in the center region (region where an absorbent member is disposed) in the width direction of the front waist member to partially decrease widthwise stretching of the elastic member, and maintain the absorber to be flat as much as possible. Thus, an effective absorbing width of the absorber can be increased (see JP2014-221122 A).

Related Art Document

[Patent document 1] JP 2014-221122 A

SUMMARY

However, the pants-type diaper having the cut portion of the elastic member includes breakage of a sheet that forms the front waist member. A broken trace of the sheet is easily recognizable by sight by a user, because the pants-type diaper has no wrinkles of the elastic member in the center region in the width direction of the front waist member. Thus, the user may easily misjudge that the pants-type diaper is a defective product.

It is an object of the present invention to provide a pants-type diaper capable of increasing an effective width of an absorber and decreasing visibility of a broken trace of a sheet in a waist member.

A first feature of the present invention is summarized as a method of manufacturing a pants-type diaper, the pants-type diaper including a front waist member, a back waist member, an absorbent body extending over the front waist member and the back waist member, and an absorber disposed in the absorbent body, the method comprising:

a step (A) of conveying a first continuous sheet in a conveyance direction, the first continuous sheet constituting at least one of the front waist member and the back waist member;

a step (B) of laminating a plurality of continuous elastic bodies along the conveyance direction on an inner side of the first continuous sheet at predetermined intervals in a crossing direction orthogonal to the conveyance direction, laminating a second continuous sheet, and bonding at least a part of the continuous elastic bodies and the second continuous sheet in the conveyance direction;

a step (C) of cutting a part of continuous elastic bodies from an outer side of the second continuous sheet or an outer side of the first continuous sheet; and a step (D) of disposing the absorbent body so as to arrange the absorber in a predetermined region, wherein in the step (C), a part of the continuous elastic bodies that is not bonded to the first continuous sheet, is cut in a region for forming the pants-type diaper, the region other than a predetermined region for arranging the absorber.

DESCRIPTION OF EMBODIMENTS

First Embodiment

A method of manufacturing a pants-type diaper 1 according to a first embodiment of the invention will be described below by referring to FIGS. 1 to 6.

In the drawings, the same or similar parts are indicated by the same or similar reference signs. The drawings are illustrated schematically and dimensional ratio and other variables differ from those of actual measurements.

The actual measurements or the like, therefore, should be determined by referring to the following description. Needless to say the drawings have different relationships or ratios of measurements.

Figure 1:
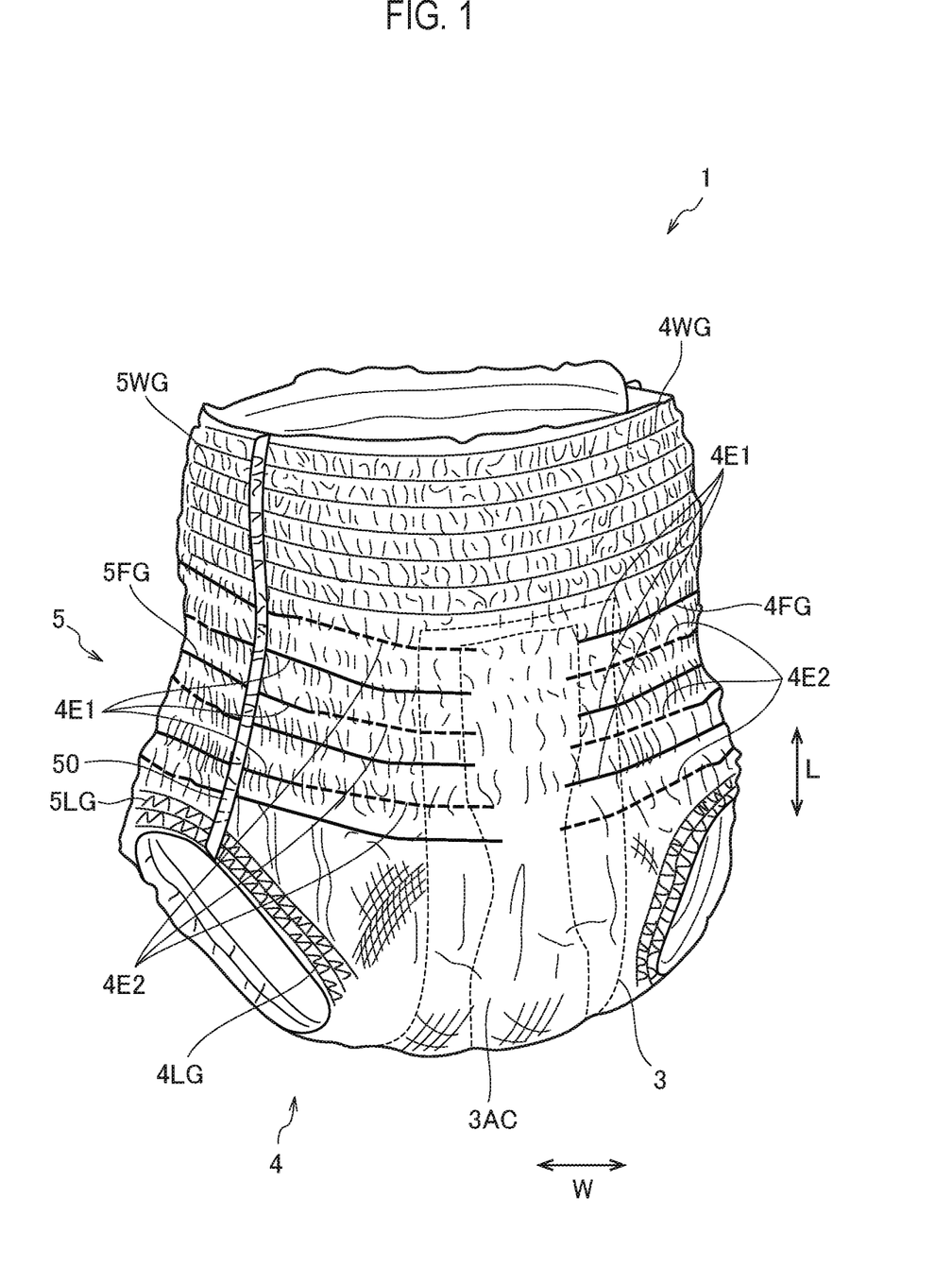
FIG. 1 is an outside view of an example of a pants-type diaper according to a first embodiment of the invention.

As illustrated in FIG. 1, the pants-type diaper 1 according to the embodiment includes a front body piece (front waist member) 4, a back body piece (back waist member) 5, and an interior part (absorbent body) 3 extending over the front body piece 4 and the back body piece 5, and an absorbent core (absorber) 3AC disposed in the interior part 3.

The pants-type diaper 1 according to the embodiment also includes a plurality of elastic members 4WG, 4FG, and 4LG arranged at predetermined intervals in a longitudinal direction L in the front body piece 4, and a plurality of elastic members 5WG, 5FG, and 5LG arranged at predetermined intervals in the longitudinal direction L in the back body piece 5.

The elastic members 4WG and 5WG are elastic members that constitute waist gathers. The elastic members 4FG and 5FG are elastic members that constitute fit gathers. The elastic members 4LG and 5LG are elastic members that constitute leg gathers.

The pants-type diaper 1 according to the embodiment is configured such that the elastic member 4FG and 5FG are not provided, at least in the front body piece 4 or the back body piece 5, partially in a region where the absorbent core 3AC is disposed.

The pants-type diaper 1 according to the embodiment also includes a stretching portion 4E1 on both sides of the region, in which the absorbent core 3AC is disposed, outwardly beyond side edges of the region in the width direction W in the front body piece 4. The stretching portion 4E1 is the region in which the elastic member 4FG can stretch. In the stretching portion 4E1, the elastic member 4FG is at least bonded to a backsheet 4B of the front body piece 4.

Meanwhile, the pants-type diaper 1 according to the embodiment includes a non-stretching portion 4E2, in which the elastic member 4FG is not able to stretch, inside the region, in which the absorbent core 3AC is disposed, inwardly from side edges of the region in the front body piece 4 in the width direction W.

The non-stretching portion 4E2 in which the elastic member is not able to stretch refers to a portion in which the elastic member 4FG is not fixedly disposed in a stretched state, although the elastic member 4FG is not regarded as being stretched until a stretching rate reaches about 10%. The stretching rate is determined as follows. A portion of the pants-type diaper 1 in which the elastic member 4FG is maximally stretched and fixed until no wrinkles are found in both lengthwise and widthwise. In this state, a predetermined length A mm in the width direction W of the pants-type diaper 1 of the entire member overlapping the elastic member 4FG is taken out. From the taken-out portion, only the elastic member 4FG is immersed, for example, in toluene, and taken out. After drying, a length B mm is measured. Thus, the stretching rate (A/B×100−100)% is determined. A negative stretching rate would be regarded as zero stretching rate. In other words, the elastic member 4FG is not bonded to a topsheet 4T and a backsheet 4B of the front body piece 4 in a stretched state in the non-stretching portion 4E2.

A method of manufacturing the pants-type diaper 1 according to the embodiment will be described by referring to FIGS. 2 to 6.

Figure 2:
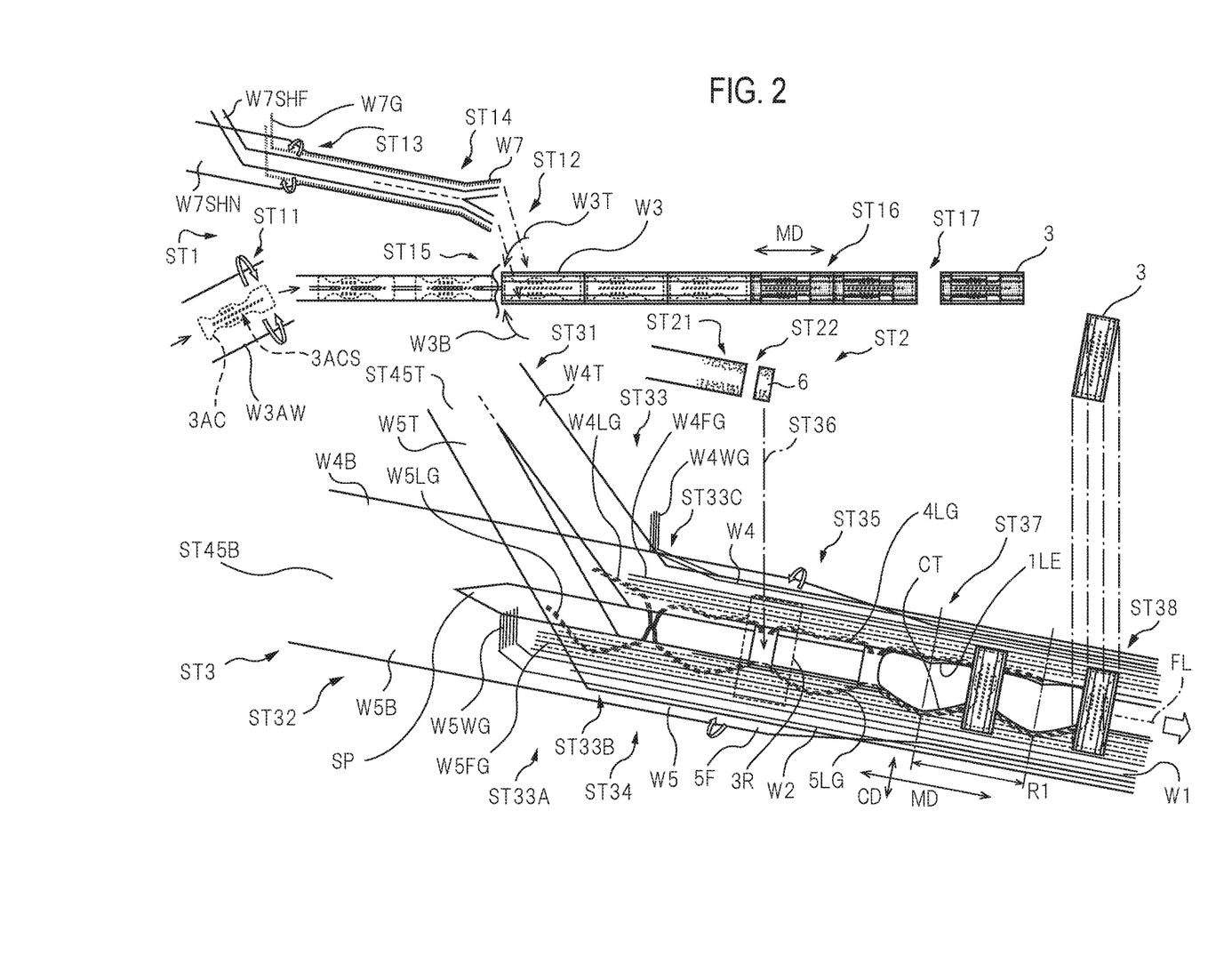
FIG. 2 is an explanatory view for explaining an example method of manufacturing the pants-type diaper according to the first embodiment of the invention.

As illustrated in FIG. 2, a method of manufacturing the pants-type diaper 1 includes a step ST1 for manufacturing the interior part 3 including a leakage preventing member, a step ST2 for manufacturing a connecting sheet 6, and a step ST3 for manufacturing a diaper web W1 which is a continuous body of the pants-type diaper 1.

At ST11 of the step ST1, the absorbent core 3AC having a previously-formed slit 3ACS is wrapped by a wrap sheet web W3AW which is a continuous body of a wrap sheet 3AW. The absorbent core 3AC is conveyed so that the slit SACS is in parallel with a conveyance direction MD.

At ST12, a topsheet web W3T and a backsheet web W3B which respectively are a continuous body of the topsheet 3T and a continuous body of the backsheet 3B are adhered to the top face and the bottom face, respectively, of the wrap sheet web W3AW wrapping the absorbent core 3AC. Thus, an interior part web (absorbent body web) W3 which is a continuous body of the interior part 3 is formed.

At ST13, a leakage-preventing film web W7SHF which is a continuous body of two parts of a leakage-preventing film 7SHF, and a continuous elastic body W7G which is a continuous body of an elastic member 7G are attached to a leakage-preventing non-woven fabric W7SHN which is a continuous body of two parts of a leakage-preventing non-woven fabric 7SHN.

At ST14, the leakage-preventing non-woven fabric web W7SHN is divided in the conveyance direction MD to form leakage preventing member webs W7 which is a continuous body of the leakage-preventing member 7. At ST15, the leakage preventing member webs W7 are attached to the back face of the interior part web W3, that is, the backsheet web W3B.

At ST16, a hot melt adhesive (HMA) is applied in a predetermined pattern to back surfaces of the interior part web W3 and the leakage preventing member webs W7, that is, a surface facing the exterior part web W2. At ST17, the interior part web W3 and the leakage preventing member webs W7 are cut to a size of a product piece to form an absorbent body 3 including the leakage preventing member 7.

At ST21 of the step ST2, the HMA is applied to the bottom surface of the connecting sheet web W6, which is a continuous body of the connecting sheet 6. At ST22, the connecting sheet web W6 is cut to a size of a product piece to form a connecting sheet 6.

At ST31 of the step ST3, a topsheet web ST45T is divided in the conveyance direction MD to form a topsheet web (second continuous sheet) W4T, which is a continuous body of the topsheet 4T of the front body piece 4, and to form a topsheet web (second continuous sheet) W5T, which is a continuous body of the topsheet 5T of the back body piece 5. Similarly, at ST32, a backsheet web ST45B is divided in the conveyance direction MD to form a backsheet web (first continuous sheet) W4B, which is a connected body of the backsheet 4B of the front body piece 4, and to form a backsheet web (first continuous sheet) W5B, which is a continuous body of the backsheet 5B of the back body piece 5. The topsheet web W4T and the backsheet web W5B are apart from each other across a separated region SP in a crossing direction CD that substantially crosses the conveyance direction MD, and are conveyed in the conveyance direction MD.

At ST33, continuous elastic bodies W4WG and W5WG, which respectively are continuous bodies of the elastic members 4WG and 5WG, and continuous elastic bodies W4FG and W5FG, which respectively are continuous bodies of the elastic members 4FG and 5FG, are attached to the backsheet webs W4B and W5B, with each web being stretched in the conveyance direction MD, at predetermined intervals in the crossing direction CD.

At ST33, at least part of the continuous elastic body W4FG (or the same shall apply to W4LG hereinafter) is bonded to the inner side of the backsheet web W4B or the inner side of the topsheet web W4T of the front body piece 4. At least part of the continuous elastic body W5FG (or the same shall apply to W5LG hereinafter) is bonded to the inner side of the backsheet web W5B of the back body piece 5.

For example, an adhesive agent (first adhesive agent) may previously be applied to the inner side of the backsheet web W4B or the inner side of the topsheet web W4T in the conveyance direction MD to allow at least a part of the continuous elastic body W4FG to be bonded to the inner side of the backsheet web W4B or the inner side of the topsheet web W4T.

The first adhesive agent may be applied previously to a position where the continuous elastic body W4FG is fixed to the backsheet web W4B or the topsheet web W4T in a region other than the predetermined region in the conveyance direction MD.

The first adhesive agent may not be applied to a region where the continuous elastic body W4FG is to be partially cut.

Alternatively, the adhesive agent may be applied to at least a part of the continuous elastic body W4FG, and such a continuous elastic body W4FG may be laminated on and bonded to the inner side of the backsheet web W4B or the inner side of the topsheet web W4T. The adhesive agent may not be applied to a part where the continuous elastic body W4FG is to be cut.

Figure 3:
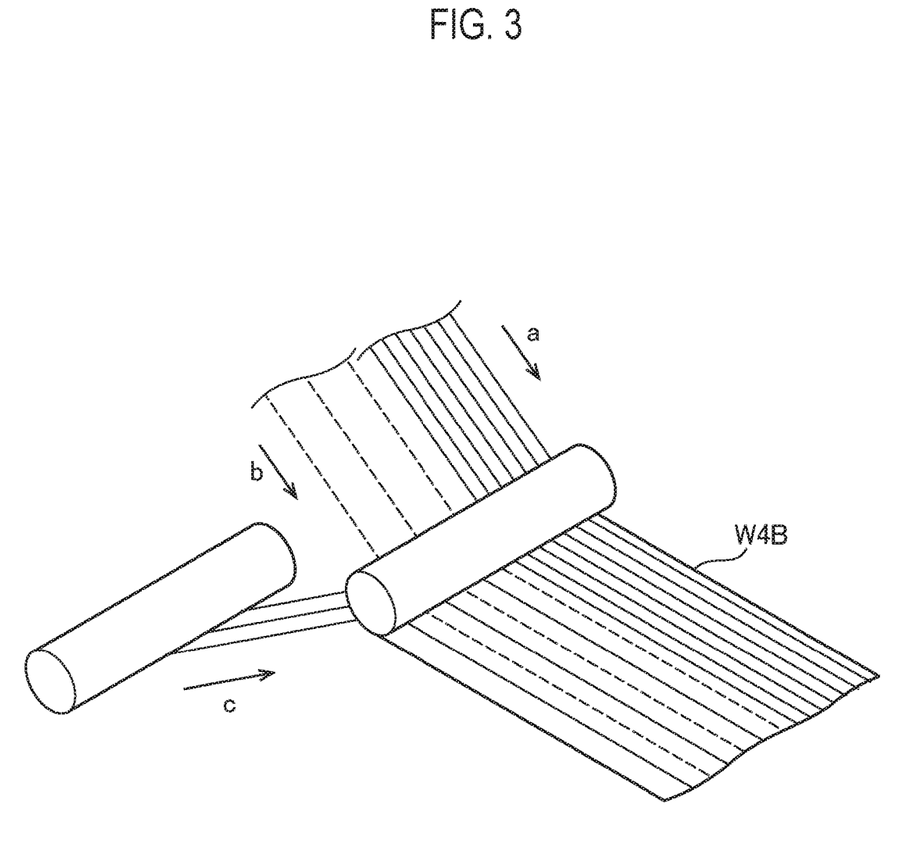
FIG. 3 is an explanatory view for explaining the example method of manufacturing the pants-type diaper according to the first embodiment of the invention.

As illustrated in FIG. 3, at least two application patterns of the adhesive agent (HMA) are provided by separately applying the HMA to the continuous elastic body W4FG and introducing the continuous elastic body W4FG from a plurality of positions (two positions) b and c.

In the example of FIG. 3, the adhesive agent is applied over the entire length of the continuous elastic body W4WG that is introduced from the position a, but the adhesive agent is not applied over the entire length of the continuous elastic body W4FG that is introduced from the positions b and c.

Lengths of the adhesive agents for applying to each continuous elastic body 4FG introduced from the positions b and c is applied can be individually adjusted. Application timing of the adhesive agent or a bonding position of the adhesive agent can also be changed for each continuous elastic body.

For example, the adhesive agent may be applied to the continuous elastic body W4FG introduced from the position b as follows. The application of the adhesive agent starts from a part corresponding to the rear side edge in the conveyance direction MD of a predetermined region 3R in the region K for forming a pants-type diaper 1. The application of the adhesive agent continues across a part corresponding to a bonded portion (side seal portion) 50, which will be described later. The application of the adhesive agent ends when the adhesive agent reaches the bonded portion 50 located in the front part in the conveyance direction MD of the next region R for forming the next pants-type diaper 1. The end position of the applied adhesive agent can be adjusted according to cutting portions of the continuous elastic body W4FG, which will be described later.

Meanwhile, the adhesive agent may be applied to the continuous elastic body W4FG introduced from the position c as follows. The application of the adhesive agent starts from a part corresponding to the bonded portion 50 located in the rear part in the conveyance direction MD in the region R for forming the pants-type diaper 1. The application of the adhesive agent ends when the adhesive agent reaches a part corresponding to the front edge in the conveyance direction MD of the predetermined region 3R in the next region R for forming the next pants-type diaper 1. The start position of applying the adhesive agent can be adjusted based on cutting portions of the continuous elastic body W4FG, which will be described later.

According to the method of manufacturing the pants-type diaper 1 of the embodiment, the plural continuous elastic bodies W4FG (or W5FG) that are laminated at predetermined intervals in the crossing direction CD are bonded to the backsheet web W4B (or W5B) or the topsheet web W4T (or W5T) in the conveyance direction MD. The bonding lengths (the positions in the conveyance direction MD) of the continuous elastic bodies on which the adhesive agent is applied can be changed.

Figure 5:
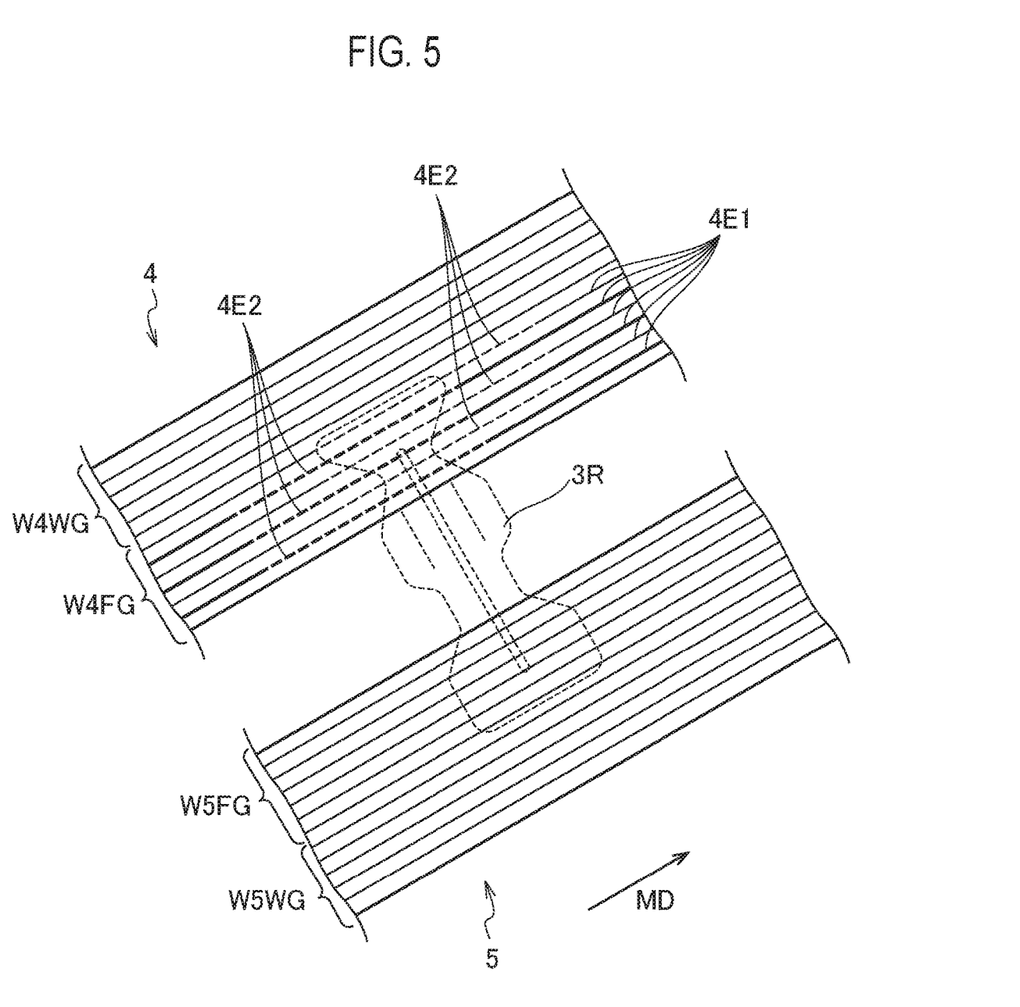
FIG. 5 is an explanatory view for explaining the example method of manufacturing the pants-type diaper according to the first embodiment of the invention.

FIG. 5 illustrates an example state of the continuous elastic bodies W4WG, W5WG, W4FG, and W5FG attached to the back sheet webs W4B and W5B at ST33. In the example of FIG. 5, the continuous elastic bodies W4WG, W5WG, W4FG, and W5FG that are indicated in bold lines are bonded to the backsheet webs W4B and W5B. The continuous elastic bodies W4WG, W5WG, W4FG, and W5FG that are indicated in dotted lines are not bonded to the backsheet webs W4B and W5B.

At ST33A, continuous elastic bodies W4LG and W5LG, which individually represent the continuous body of the elastic bodies 4LG and 5LG, are stretched and attached to the topsheet webs W4T and W5T.

In this case, the continuous elastic bodies W4LG and W5LG are partially disposed on the topsheet webs W4T and W5T, respectively. The other parts of the continuous elastic bodies W4LG and W5LG are disposed within a separated region SP, that is, outside the topsheet webs W4T and W5T.

At ST33B, the topsheet webs W4T and W5T are disposed on the backsheet webs W4B and W5B, respectively. Specifically, the topsheet webs W4T and W5T are laminated on the internal surfaces of the backsheet webs W4B and W5B. As a result, the continuous elastic bodies W4WG, W4FG, W4LG, W5WG, W5FG and W5LG are sandwiched between the backsheet webs W4B and W5B and the topsheet webs W4T and W5T.

An adhesive agent (second adhesive agent) is previously applied to the backsheet webs W4B and W5B to bond the backsheet webs W4B and W5B with the interior part 3 (or the topsheet webs W4T and W5T). The adhesive agent is applied at least in the predetermined region 3R. The predetermined region 3R is a region where the absorbent core 3AC is to be disposed in a subsequent step.

A basis weight (weight per square) of the second adhesive agent may be smaller than a basis weight of the first adhesive agent. Thus, the continuous elastic bodies W4FG and W5FG are strongly bonded to the backsheet webs W4B and W5B and the topsheet webs W4T and W5T in the region where the first adhesive is applied. At the same time, the predetermined region 3R where only the second adhesive is applied can maintain flexibility.

Other bonding methods known in the art, such as heat sealing, can also be used other than the adhesive agents described above.

The continuous elastic bodies W4FG, W5FG and the topsheet webs W4T, W5T may simultaneously be laminated on and bonded to the inner side of the backsheet webs W4B, W5B.

At ST33C, portions P4 and P5 of the continuous elastic bodies W4LG, W5LG located in the separated region SP are cut.

At ST34, the backsheet webs W4B and W5B and the topsheet webs W4T and W5T are pressed together to form the front body piece web W4 and the back body piece web W5 which are the continuous bodies of the front body piece 4 and the back body piece 5, respectively.

In the front body piece 4, a portion of the continuous elastic body W4FG is cut from the outer side of the topsheet web W4T or the backsheet web W4B. Alternatively, a portion of the continuous elastic body W5FG may be cut from the outer side of the topsheet web W5T or the backsheet web W5B in the back body piece 5.

Figure 4:
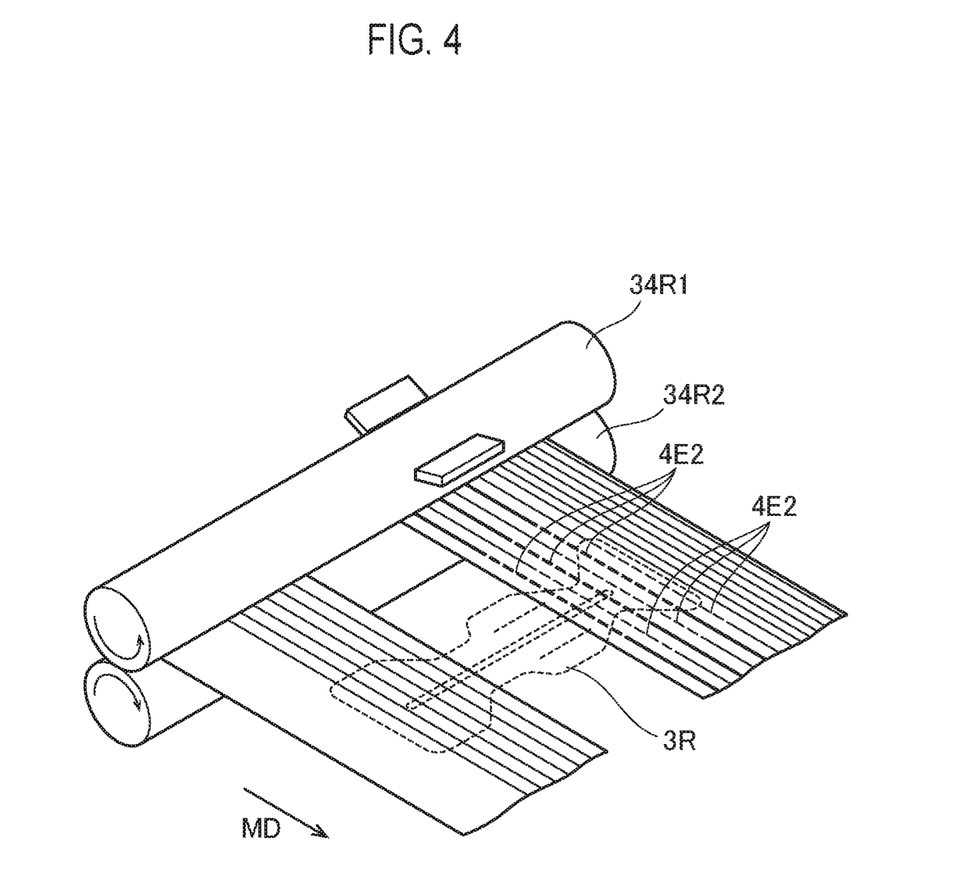
FIG. 4 is an explanatory view for explaining the example method of manufacturing the pants-type diaper according to the first embodiment of the invention.

For example, the continuous elastic body W4FG may be partially cut by rollers 34R1 and 34R2 including projecting blades (cutting blades), as illustrated in FIG. 4. The roller 34R1 may have a projecting blade capable of cutting plural continuous elastic bodies W4FG together, as illustrated in FIG. 4. The roller 34R1 may have a projecting blade for each continuous elastic body W4FG.

In the front body piece 4 or the back body piece 5, the cutting blades may be provided, one each for the continuous bodies W4FG and W5FG, for cutting each one of the continuous elastic body W4FG or W5FG at least in the center region in the crossing direction CD of the region where the continuous elastic body W4FG or W5FG to be cut is disposed relative to the conveyance direction MD. This structure particularly minimizes the cut trace in the center region in the crossing direction CD where the cut trace is easily distinguishable.

The projecting blades may be provided at a predetermined angle (e.g., 5 to 175 degrees) relative to the conveyance direction MD, instead of a vertical angle, to facilitate transmission of pressure to the continuous elastic body W4FG and decrease friction with the continuous elastic body W4FG. The cut trace would be shorter and less distinguishable in the crossing direction CD if the predetermined angle is near a vertical direction relative to the conveyance direction MD.

Alternatively, the continuous elastic body W4FG may be cut by forming a penetrating hole in the topsheet web W4T. The continuous elastic body W4LG may only be cut by heat fusion without making the hole on the topsheet Web W4T, or during fusion bonding of the topsheet web W4T and the backsheet web W4B. The continuous elastic body W4LG may also be cut only by pressure.

Specifically, the part of the continuous elastic body W4FG (non-stretching portion 4E2) which is not bonded to the backsheet web W4B is cut in the region other than the predetermined region 3R of the region R for forming one pants-type diaper 1.

The part of the continuous elastic body W4FG (non-stretching portion 4E2) may be cut both in the front side region and rear side region in the region R for forming one pants-type diaper 1, the front side region positioned downstream of the predetermined region 3R, the rear side region positioned upstream of the predetermined region 3R.

Alternatively, the part of the continuous elastic body W4FG (non-stretching portion 4E2) may be cut, only in the front side region or the rear side region in the region R for forming one pants-type diaper 1, the front side region positioned downstream of the predetermined region 3R, the rear side region positioned upstream of the predetermined region 3R.

This structure eliminates an inconvenience of aesthetically damaging the appearance of the pants-type diaper 1 due to shreds of the continuous elastic body W4FG left after cutting in the near-center of the region R for forming one pants-type diaper 1.

A portion in which each of the continuous elastic bodies W4FG arranged in the crossing direction CD is partially cut may change alternately between the front, side region and the rear side region. This structure achieves an effect of distributing the cut trace in the crossing direction CD and making the cut trace less distinguishable.

The stretching portion 4E1 may also be cut, in addition to the non-stretching portion 4E2, at least in the front side region or the rear side region of the redetermined region 3R in the conveyance direction MD of the region R for forming one pants-type diaper 1. Any problem would not occur because the stretching characteristic of the continuous elastic body W4FG that constitutes the stretching portion 4E1 (that is, the continuous elastic body W4FG bonded to the backsheet web W4B) is maintained.

Figure 6:
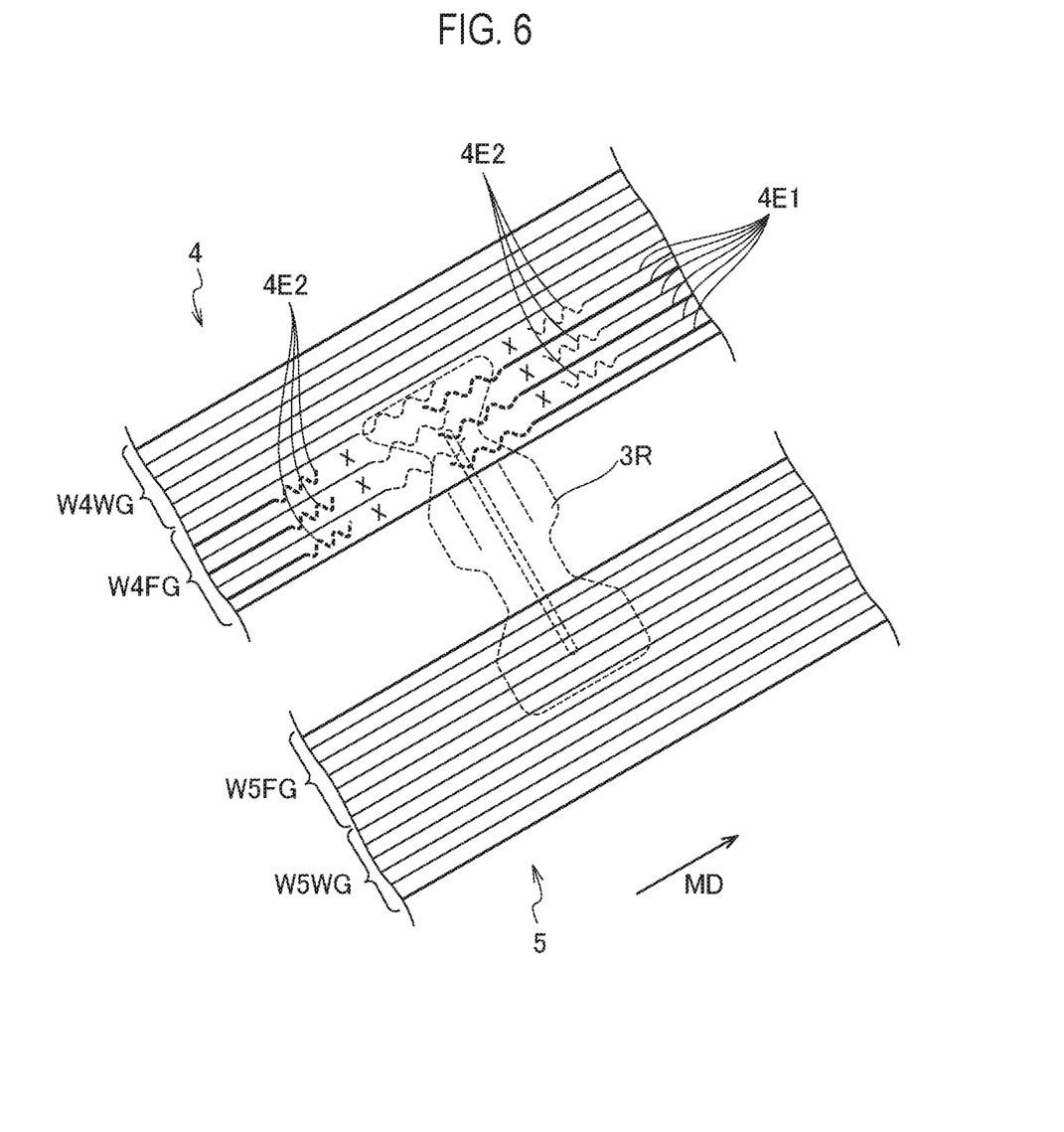
FIG. 6 is an explanatory view for explaining the example method of manufacturing the pants-type diaper according to the first embodiment of the invention.

FIG. 6 illustrates an example state in which the continuous elastic body W4FG is partially cut. In the example of FIG. 6, each continuous elastic body W4FG is cut with a single projecting blade. In the example of FIG. 6, the cutting parts of the individual members of the continuous elastic body W4FG arranged in the crossing direction CD is shifted in the conveyance direction MD.

The continuous elastic body W4FG may be cut before or after ST37, or after ST38. Both ST37 and ST38 will be described later. Alternatively, the cutting step may be executed simultaneously at ST37. To achieve this, a cutting blade for cutting the continuous elastic body W4FG is installed on the roller having a cutting blade for defining a leg hole 1L. This eliminates the need for additional space and decreases the cost.

At ST35, outer edges of the backsheet webs W4B and W5B are folded to provide a folded portion 5F. ST35 may be executed after ST38.

At ST36, the connecting sheets 6 are attached to the front body piece web W4 and the back body piece web W5 over the separated region SP at intervals in the conveyance direction MD, and thus the exterior part web W2 that is a continuous body of the exterior part 2 is formed.

To sandwich the periphery of both ends of the connecting sheet 6 in a longitudinal direction LN between the topsheets 4T, 5T and the backsheets 4B, 5B, the connecting sheet 6 is first attached to the topsheet webs W4T and W5T, and the backsheet webs W4B and W5B are then overlapped on the connecting sheet 6 and the topsheet webs W4T and W5T. Alternatively the connecting sheet 6 may be first attached to the backsheet webs W4B and W5B, and the topsheet webs W4T and W5T are then overlapped on the connecting sheet 6 and the backsheet webs W4B and W5B.

At ST37, the exterior part web W2 is cut at intervals in the conveyance direction MD to form an edge 1LE that defines the leg hole 1L. The front body piece web W4 and the back body piece web W5 may be cut along the elastic members 4LG and 5LG.

The connecting sheet 6 is cut in such a manner that both side edges 6S of the connecting sheet 6 are curved inward or at least part of both side edges 6S of the connecting sheet 6 are located inside of both side edges 3S of the interior part 3 in a lateral direction LT in the separated region SP. The cutting step is executed once, for example, along a circular cutting line CT. Remains of trimming are collected.

At ST38, the interior part 3 including the leakage preventing member is attached to the front body piece web W4, the back body piece web W5 and the connecting sheet 6, and thus the diaper web W1 is formed. A guide is preferably provided to dispose the exterior part web W2 at a proper position in the crossing direction CD immediately before cutting or attaching of the interior part 3.

Subsequently, the diaper web W1 is folded (not illustrated) along a folding line FL in the conveyance direction MD. The folding line FL may be provided in the center of the crossing direction CD of the diaper web W1, or may be provided out of the center of the crossing direction CD of the diaper web W1.

The front body piece W4 and the back body piece W5 are partially bonded at intervals in the conveyance direction MD to form the bonded portion 50. Specifically, the front body piece web W4 (first continuous sheet) and the back body piece web W5 (second continuous sheet) are bonded together at both the front side edge and the rear side edge of each region R for forming one pants-type diaper 1 in the conveyance direction MD.

Lastly the diaper web W1 is cut (which is not illustrated) in the crossing direction CD at the bonded portion 50 to complete the pants-type diaper 1.

The method of manufacturing the pants-type diaper 1 according to the embodiment enables the continuous elastic body W4FG to be cut in a region other than the region where the absorbent core SAC is disposed in the front body piece 4 (or the back body piece 5), thereby allowing the cut trace to be less distinguishable.

The method of manufacturing the pants-type diaper 1 according to the embodiment also enables the stretching portions 4E1 to have different lengths in the longitudinal direction L, so that the stretching portions 4E1 can be enlarged at crotch portion of a wearer of the pants-type diaper 1 by adjusting the position of the inner ends of the stretching portions 4E1. This increases the range of applicable sizes of the pants-type diaper 1 and achieves both easiness and fitting sense of wearing. The embodiment can decrease the length of the cutting portion if the cutting portion partially extends over the side portions of the absorbent core 3AC in the width direction, allowing the cut trace to be less indistinguishable.

Further, the method of manufacturing the pants-type diaper 1 according to the embodiment enables the second adhesive agent to be applied to the predetermined region 3R to eliminate floating between the topsheet web W4T and the backsheet web W4B, thereby preventing break of the sheets during using and improving the external appearance of the pants-type diaper 1.

The present application incorporates by reference the entirety of Japanese Patent Application Number 2015-190129, filed Sep. 28, 2015.

INDUSTRIAL APPLICABILITY

As described above, the present invention provides the method of manufacturing the pants-type diaper capable of increasing the effective absorbing width of the absorbent member and allowing the cut trace in the sheet of the waist members to be less distinguishable.

What is claimed is:

1. A method of manufacturing a pants-type diaper, the pants-type diaper including a front waist member, a back waist member, an absorbent body extending over the front waist member and the back waist member, and an absorber disposed in the absorbent body,
the method comprising:
a step (A) of conveying a first continuous sheet in a conveyance direction, the first continuous sheet constituting at least one of the front waist member and the back waist member;
a step (B) of laminating a plurality of continuous elastic bodies along the conveyance direction on an inner side of the first continuous sheet at predetermined intervals in a crossing direction orthogonal to the conveyance direction, laminating a second continuous sheet, and bonding at least a part of the continuous elastic bodies and the second continuous sheet in the conveyance direction;
a step (C) of cutting a part of continuous elastic bodies from an outer side of the second continuous sheet or an outer side of the first continuous sheet; and
a step (D) of disposing the absorbent body so as to arrange the absorber in a predetermined region, wherein
in the step (C), a part of the continuous elastic bodies that is not bonded to the first continuous sheet is cut in a region for forming the pants-type diaper, the region other than a predetermined region for arranging the absorber.

2. The method of manufacturing the pants-type diaper according to claim 1, wherein
in the step (C), the part of the continuous elastic bodies is cut in both a front side region and a rear side region, the front side region positioned downstream of the predetermined region, the rear side region positioned upstream of the predetermined region.

3. The method of manufacturing the pants-type diaper according to claim 1, wherein
in the step (B), bonding lengths of the continuous elastic bodies laminated at the predetermined intervals in the crossing direction is changed each other.

4. The method of manufacturing the pants-type diaper according to claim 1, further comprising:
a step of bonding the first continuous sheet and the second continuous sheet each other at a front side edge and a rear side edge in the conveyance direction of the region for forming the pants-type diaper.

5. The method of manufacturing the pants-type diaper according to claim 1, wherein
in the step (C), the part of the continuous elastic bodies is cut only in a front side region or a rear side region, the front side region positioned downstream of the predetermined region, the rear side region positioned upstream of the predetermined region.

6. The method of manufacturing the pants-type diaper according to claim 5, wherein
in the step (C), an each part in which each of the continuous elastic bodies arranged in the crossing direction is cut changes alternately between the front side region and the rear side region.

7. The method of manufacturing the pants-type diaper according to claim 1, wherein
in the step (B), the continuous elastic bodies are laminated on the inner side of the first continuous sheet or an inner side of the second continuous sheet in a state where an adhesive agent is applied to the continuous elastic bodies at least partially.

8. The method of manufacturing the pants-type diaper according to claim 7, wherein
the adhesive agent is not applied to the part of the continuous elastic bodies that are to be cut in the step (C).

9. The method of manufacturing the pants-type diaper according to claim 1, further comprising:
a step (E) of applying a first adhesive agent to a position at which the continuous elastic bodies are fixed on the first continuous sheet or the second continuous sheet in the conveyance direction in the region other than the predetermined region; and
a step (F) of applying a second adhesive agent at least in the predetermined region.

10. The method of manufacturing the pants-type diaper according to claim 9, wherein
a basis weight of the second adhesive agent is smaller than a basis weight of the first adhesive agent.

11. The method of manufacturing the pants-type diaper according to claim 9, wherein
in the step (E), the first adhesive agent is not applied to the part to be cut in the step (C).

12. The method of manufacturing the pants-type diaper according to claim 1, wherein
in the step (C), the part of the continuous elastic bodies are cut by a cutting blade, and
at least one cutting blade for cutting one of the continuous elastic bodies is provided at least in a center region in the crossing direction.

* * * * *